United States Patent
Tung et al.

(10) Patent No.: US 6,627,459 B1
(45) Date of Patent: Sep. 30, 2003

(54) IMMUNOASSAY CONTROLS

(75) Inventors: Ker-kong Tung, Del Mar, CA (US); He Huang, San Diego, CA (US)

(73) Assignee: Applied Biotech, Inc., San Diego, CA (US)

( * ) Notice: Subject to any disclaimer, the term of this patent is extended or adjusted under 35 U.S.C. 154(b) by 0 days.

(21) Appl. No.: 09/552,397

(22) Filed: Apr. 19, 2000

(51) Int. Cl.$^7$ .............................................. G01N 33/558
(52) U.S. Cl. ........................ 436/514; 422/55; 422/56; 422/57; 435/7.1; 435/7.2; 435/7.21; 435/7.32; 435/7.92; 435/287.1; 435/287.2; 435/87.2; 435/287.9; 435/805; 435/810; 435/970; 436/169; 436/518; 436/530; 436/810
(58) Field of Search ...................... 422/55–58; 435/7.1, 435/7.2, 7.21, 7.32, 7.92, 287.1, 287.9, 805, 810, 970; 436/169, 514, 518, 530, 810

(56) References Cited

U.S. PATENT DOCUMENTS

| | | | | |
|---|---|---|---|---|
| 5,081,013 A | * | 1/1992 | Rovelli et al. .............. | 435/7.92 |
| 5,354,692 A | * | 10/1994 | Yang et al. .................. | 436/514 |
| 5,356,782 A | | 10/1994 | Moorman et al. | |
| 5,384,264 A | * | 1/1995 | Chen et al. .................. | 436/525 |
| 5,712,172 A | * | 1/1998 | Huang et al. ................ | 436/518 |
| 5,714,389 A | | 2/1998 | Charlton et al. ............. | 436/514 |
| 6,027,943 A | * | 2/2000 | Kang et al. .................. | 436/518 |
| 6,046,058 A | | 4/2000 | Sun | |
| 6,187,598 B1 | * | 2/2001 | May et al. .................... | 436/514 |
| 6,194,221 B1 | * | 2/2001 | Rehg et al. .................. | 436/514 |
| 6,194,225 B1 | * | 2/2001 | Oka et al. .................... | 436/518 |
| 6,221,625 B1 | * | 4/2001 | Ashihara et al. ............. | 435/7.9 |
| 6,248,596 B1 | * | 6/2001 | Durst et al. .................. | 436/518 |
| 6,248,598 B1 | * | 6/2001 | Bogema ..................... | 436/518 |
| 6,277,650 B1 | * | 8/2001 | Nazareth et al. ............. | 436/514 |

* cited by examiner

Primary Examiner—Christopher L. Chin
(74) Attorney, Agent, or Firm—Wood, Herron & Evans, L.L.P.

(57) ABSTRACT

A device and method for performing a rapid immunoassay for a biological analyte containing a positive control analyte which is concurrently tested using the same device and immunochemical reaction as the biological analyte. The positive control analyte is non-crossreactive with the biological analyte to be detected and may be an immunogen or a hapten. The device and method permit operators of the test device, particularly non-laboratory professionals, to determine that an assay is performed correctly and that the device is functioning properly, thereby allowing the operator to have confidence in the accuracy of either a positive or negative result. This is particularly important when a positive result is indicated by the absence of color at a test site, which is counterintuitive with many operators and which frequently occurs with a competitive immunoassay.

11 Claims, 1 Drawing Sheet

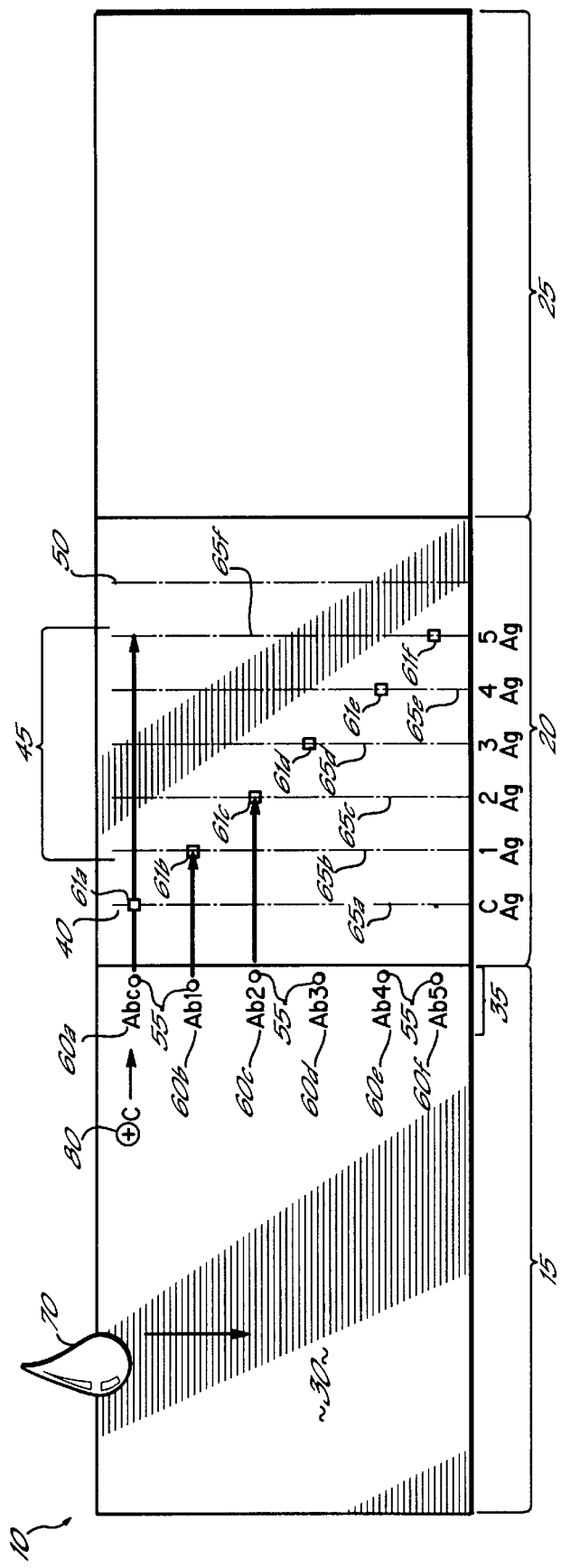

IMMUNOASSAY CONTROLS

FIELD OF THE INVENTION

The invention is directed generally to controls used with point of care immunological tests.

BACKGROUND OF THE INVENTION

Many types of qualitative and/or quantitative assays that were once performed only by trained technical personnel are now routinely performed by individuals having either no training or less than optimal training in specific laboratory procedures and techniques. As one example, medical professionals such as nursing staff frequently perform point of care patient tests, yet frequently lack familiarity with the nuances of these analytical procedures. Such a lack of familiarity can lead to inaccurate test performance because of oversight, technical errors, unfamiliarity with the test procedure, etc. As another example, many types of rapid assay test kits are available for over the counter purchase and home use. In these instances, testing is performed by individuals having no laboratory training whatsoever.

For the above reasons, many point of care tests incorporate the use of an analyte or chemical that will yield a pre-determined result if the assay is performed correctly, known simply as a control specimen or a control. In laboratory analysis, a control is defined as a substance whose composition is qualitatively and/or quantitatively known and that is subject to the same assay procedure as the sample to be tested. A detectable result is displayed, indicative of proper test function and performance, and, hence, a valid assay result. One or more controls may be assayed along with a particular test to determine different concentration ranges of an analyte (e.g., high, low and normal control levels for a particular analyte), or to provide additional assurance of test accuracy and user competence. When medical laboratories perform such tests, assay of a control is a mandatory part of the normal daily routine to ensure accurate results, and incorporation of a control is a component of virtually all state and national quality assurance programs.

One type of control is a sample known to contain a detectable level of an analyte of interest. This control is termed a positive control for the particular analyte because it is known to contain the analyte and thus will yield a positive result if a functional assay is properly performed. Assay of a positive control verifies accuracy of a procedure. However, for a point of care test where one or several tests are performed, an external positive control doubles both the cost and the time required to perform a single patient assay, since a control sample must be tested using one device and a patient sample must be tested using a second device. Additionally, the control must be purchased and stored separately, which imposes added cost and inconvenience. To overcome these drawbacks, some manufacturers have incorporated a positive control directly into the assay device, a so-called "built-in" positive control.

One general type of built-in positive control in a sandwich immunoassay may utilize a protein that is a member of a specific binding pair, such as IgG or other types of antibodies, or antigens. The protein is labeled through binding to any of various types of labels or markers (e.g., enzymes, chromophores, fluorophores, metal sols, etc.) to render it detectable, either directly or indirectly. The labeled protein is captured on a defined zone ("positive control zone") of a test device by an immobilized protein that is its specific binding partner.

One example of a test incorporating a positive control for a sandwich immunoassay is the ICON® II HCG Immuno-Concentratione™ Assay (Hybritech Inc., San Diego, Calif.) for the determination of human chorionic gonadotropin (hCG) in a sample of serum or urine. In the ICON® assay, the analyte serving as a positive control is an antibody against IgG (anti-IgG) which is immobilized at a positive control site in the test device. The immobilized anti-IgG antibody binds to IgG, present as mouse monoclonal IgG (anti-hCG) that is conjugated or labeled with alkaline phosphatase enzyme (IgG-Enz). The anti-IgG immobilizes the IgG-Enz conjugate and, when the substrate for the enzyme is added, a color forms at the positive control site. Thus, the positive control in the ICON® test is a two component complex of one antigen (IgG) and one antibody (anti-IgG), and a positive result is indicated by the presence of color at the positive control site.

Similarly, and as an example of a test incorporating a control for a competitive immunoassay, the Triage® Drugs of Abuse Panel plus Tricyclic Antidepressants (Biosite Diagnostics, San Diego, Calif.) test for urine drug detection forms a two component complex in the positive control zone. In the Triage® test, which is a competitive binding immunoassay, a labeled antigen (drug) provided as a reagent competes with drug which may be present in the patient urine sample for antibody binding sites. Labeled antigen, displaced from antibody binding sites by drug that was present in the patient sample, binds to a zone of antibody that is immobilized on the test membrane. While the composition of the positive control in the Triage® test is not disclosed by the manufacturer, it is likely a two component complex of one antigen and one antibody and a positive result is indicated by the presence of color at the positive control site. As in the ICON® test, the immunological reaction for a positive control is different from the reaction for a test sample.

Both the ICON® and the Triage® tests use the presence of a color at the positive control site as an internal assay control to indicate correct reagent addition and test performance. In competitive assays, one can assay either the labeled antigen that has bound to the antibody by measuring the amount of label in the antigen-antibody complex (bound fraction), or one can assay the labeled antigen that has not bound to the antibody by measuring the amount of label in the supernatant (free fraction). In rapid immunoassays involving a test strip or membrane, it is the bound fraction that is routinely monitored, since the test strip or membrane itself contains the bound fraction.

If analyte is absent from the sample, there will be no competition and the labeled antigen will occupy all of the limited number of antibody binding sites. If analyte is present in a sample, there will be competition and less labeled antigen will be present in the bound fraction. Thus, when analyzing the bound fraction in competitive assays, presence of analyte is indicated by the absence of color in the test site. What is needed, therefore, and what is not provided in the assays presently available, is a test incorporating a built-in positive control that generates a positive result as an absence of color, as occurs in competitive assays.

A positive control should preferably test for the presence of the same or a related analyte as that being assayed, using the same device as is used for detecting the analyte, and using the same chemistry and the same type of immunological reaction as is used for detecting the analyte. However, in competitive reactions, the presence of analyte is indicated by the absence of color formation on the test strip. Thus, a need exists for an improved positive control for point of care testing of one or more analytes in a sample which reflects the use of the same chemistry and the same type of immunological reaction as occurs for the analyte of interest.

SUMMARY

The invention is directed to a device and method of using the device in which a test strip incorporates a positive control that is identical or closely related to at least one biological analyte, and that uses same device and the same immunological reaction as is used for detecting the analyte. Such a device and method provide a more reliable indicator that the assay was functional and was correctly performed, and that an accurate result was achieved. This is particularly useful for tests performed by lay operators, for example, tests sold over-the-counter for at home use.

The invention is also directed to a test strip for immunoassay of at least one biological analyte in a patient sample where the presence of biological analyte in the sample is indicated by absence of color formation at the test site. The test strip has a conjugate pad, either as part of or separate and downstream from a sample pad, and a membrane located downstream from the conjugate pad and containing a test site. The sample pad or conjugate pad contains a mobilizable control analyte that does not cross react with the biological analyte and the conjugate pad contains a mobilizable labeled antibody to the control analyte. The membrane contains an immobile control analyte at a control site. The presence of the control analyte is indicated by absence of color formation at the control site, which is the same result as occurs for the presence of the biological analyte at the test site. The control analyte may be cotinine, creatinine, and/or digoxin, and the label may be an enzyme, a metal sol such as colloidal gold, a fluorophore, a chromophore, etc. The test strip may optionally incorporate a dye in the positive control site.

The invention is also directed to a method for testing a control analyte in a rapid immunoassay for a biological analyte in a sample where the sample, for example urine, migrates through a test strip. The sample is contacted with a sample pad, located upstream of a separate conjugate pad, or with a conjugate pad and a membrane containing a test site. The conjugate pad contains an antibody specific to each biological analyte and an antibody to the control analyte, each individually labeled. The test result is read at a test site in the membrane where a positive result for the biological analyte is an absence of color formation at the test site, and the control result is read at a control site in the membrane where a positive results for the control analyte is an absence of color formation at the control site. In one embodiment, the immunoassay is a competitive immunoassay.

The invention is also directed to a test strip for concurrently determining the presence of at least one biological analyte in a sample and a control analyte by a competitive immunoassay. The test strip has a sample pad containing a mobilizable control analyte and a mobilizable labeled antibody against the control analyte, and a downstream membrane containing a discrete region of immobilized control analyte. In one embodiment, the control analyte is cotinine and the biological analyte is at least one drug.

The invention is also directed to a method to verify an immunoassay for at least one biological analyte in a sample with a control analyte. A sample is applied to a test device which has, in sequence, a sample pad containing a mobilizable control analyte, a mobilizable labeled anti-control analyte antibody, at least one labeled mobilizable anti-biological analyte antibody, and a downstream membrane containing a region of immobilized control analyte and a separate region of at least one immobilized biological analyte. The sample is contacted with the device and the results for the biological analyte are determined at a test site on the membrane and the results for the control analyte are determined at a control site on the membrane to verify the biological analyte immunoassay.

These and other embodiments will be apparent with further reference to the following figure and detailed description.

BRIEF DESCRIPTION OF THE FIGURE

The FIGURE is a schematic view of a test strip incorporating a control in which absence of color indicates a positive result.

DETAILED DESCRIPTION

A rapid immunoassay device and method which uses the identical device, the identical immunochemical reaction, and the identical or a closely related analyte to the analyte of interest to test for both the biological analyte or analytes of interest and a control analyte is disclosed. A biological analyte is any analyte present in a biological sample and for which a clinical test is appropriate for qualitative and/or quantitative determination. The biological analyte may an endogenous substance such as a protein (e.g., human chorionic gonadotropin) or a hormone (e.g., luteinizing hormone), or an exogenous substance such as a drug or drug metabolite (e.g., cocaine or other drugs of abuse and/or their metabolites) or a bacterial antigen (e.g., Streptococcus), or a combination. In a competitive assay, the biological analyte is frequently one or more drugs of abuse and/or their metabolites. A control analyte is one which should not cross react with the biological analyte, not be routinely assayed in a rapid immunoassay test strip format, and should not affect the assay of interest. In the device and method, a positive result is indicated for both the biological analyte and the positive control analyte by the absence of color formation at the test site and positive control site, respectively.

With reference to the FIGURE, a test strip 10 is shown. The test strip 10 has three general components in the following order of sample migration from upstream to downstream: a sample pad 15 where the sample to be tested is applied either directly or indirectly to a conjugate pad 35, a membrane 20 where the specific immunochemical reactions occur, and an absorbent pad 25 to absorb sample that has been applied. The sample pad 15 contains a sample application site 30. A downstream conjugate pad 35 may be either incorporated on a region of the sample pad 15 or may be separate from the sample pad 15. The membrane 20 contains a positive control site 40, one or more test sites 45 and optionally a negative control site 50. The positive control site 40 and optional negative control site 50 may be either upstream or downstream relative to the test site 45. The absorbent pad 25 serves as a reservoir to contain the bulk volume of the sample, typically urine, applied to the test strip 10.

The test strip 10 is composed of one or more materials that allow transport of the sample throughout the strip 10 by capillary or wicking action.

For example, the sample pad 15 may be composed of any absorbent material such as cellulose, cellulose acetate, fiberglass or rayon. However, a sample pad which contains an integral conjugate pad cannot be composed of cellulose. The membrane 20 may be composed of nylon or nitrocellulose. The absorbent pad may be composed of the same material as the sample pad 15, or may be a different material.

In assembly of the test strip 10, the sample pad 15, conjugate pad 35, membrane 20, and absorbent pad 25 are prepared and secured to a backing (not shown) following the previously described format. To prepare the sample pad 30, microgram quantities of the positive control analyte 80 are applied. To prepare the conjugate pad 35, a mixture of labels 55, each associated with either an anti-positive control antibody 60*a*, or an antibody specific to each of the one or more analytes to be tested 60*b*, 60*c*, 60*d*, 60*e*, 60*f*, etc, is applied. The label 55 may be an enzyme, a metal sol, a chromophore, and/or a fluorophore, and may directly form a visible color or may be further reacted to form a visible color. In one embodiment, the label 55 is colloidal gold. To prepare the membrane 20, the control analyte 61*a* is immobilized at the control site 65a in the membrane, and the respective antigen analyte or analytes 61*b*, 61*c*, 61*d*, 61*e*, 61*f* are immobilized, each in a discrete line or zone 65*a*, 65*b*, 65*c*, 65*d*, 65*e*, collectively comprising the test site 45.

In an optional embodiment, the positive control site 65*a* contains a marker, for example, a dye such as bromphenol blue, that serves as a marker to allow the operator to visualize the location of the positive control site on an unused test strip. In use, the dye is mobilized and will migrate along the test strip with the migrating urine sample, thus the operator viewing a test in progress will see a disappearance of a colored line at the positive control site. The migrating marker provides a level of assurance to the operator that the test strip is functional. This may be of benefit, particularly in the case where a positive result is indicated by the absence of color.

The choice of positive control analyte depends on several factors. Since antibodies to the positive control are required for the reaction, the positive control may be a immunogenic protein or may be a low molecular weight hapten, defined as a compound that is not itself immunogenic but that, after conjugation to an immunogenic compound such as a cell or carrier protein, becomes immunogenic and induces formation of an antibody, which can bind the hapten alone in the absence of carrier. Antibodies, usually monoclonal antibodies, are prepared by standard techniques known to one skilled in the art. The positive control analyte should be one that is not routinely assayed in test strips and should not crossreact with the biological analyte. In one embodiment, cotinine may be used as a positive control. In alternative embodiments, substances other than cotinine such as creatinine, digoxin, or drugs other than those to be assayed may be used, as long as they are not commonly assayed.

In one method using the above-described embodiment for assay of a panel of drugs, cotinine is used as a positive control. Cotinine (1-methyl-5-(3-pyridinyl)-2-pyrrolidinone) is a metabolite of nicotine and has a molecular weight of 176. A quantity of cotinine in the range of about 0.5 μg to 10 μg, preferably about 2 μg, is applied to the sample pad 15. The conjugate pad 35 contains gold particles 55 that are each coated with either anti-cotinine antibody 60*a*, or an antibody specific to each of the drugs in the panel to be tested 60*b*, 60*c*, 60*d*, 60*e*, 60*f*, etc. In the membrane 20 of the test strip 10, the respective drug antigens 61*b*, 61*c*, 61*d*, 61*e*, 61*f* are immobilized, each at a discrete site or line 65*a*, 65*b*, 65*c*, 65*d*, 65*e*, collectively comprising the test site 45.

In use, a liquid test sample 70 such as serum, plasma, or urine is applied to the sample pad 15 of the test strip 10. This may be accomplished by dipping the sample pad 15 into a container holding the sample to be tested, or, if the sample is urine, by exposing the sample pad 15 to a stream of urine, or by placing a specified volume of sample 70 on the sample pad 15 using a pipette or other transfer device (not shown). Alternatively, the sample may be initially applied to a wick (not shown) which is wicking contact with the sample pad region 15. By whatever method applied, the sample 70 then migrates through the regions of the test strip 10 by capillary or wicking action.

Upon reaching the conjugate pad 35, the liquid sample 70 suspends the mix of gold particles 55 in the conjugate pad 35. Each gold particle in the mix is individually coated or labeled with only one type of specific antibody, either the anti-positive control antibody 60*a*, or an anti-drug antibody that is specific for a particular analyte 60*b*, 60*c*, 60*d*, 60*e*, or 60*f*.

If the sample 70 does not contain an analyte to be tested, when the antibody-coated (e.g., 60*b*) gold particle 55 reaches the test site 45, it will bind to the corresponding antigen (e.g. 61*b*) that is immobilized at the test site 45. An antigen-antibody complex (e.g., 60*b*–61*b*) that is specific for the particular analyte is formed at a discrete region (e.g. 65*b*) of the test site 45.

Thus, a colored line or zone at this test site (e.g. 65*b*) indicates that the sample 70 does not contain the analyte of interest.

Conversely, if the sample 70 contains sufficient quantities of one or more of the analytes to be tested, the specific antibody (e.g. 60*c*) coated on the gold particles 55 binds to the analyte (antigen) in the sample 70 and saturates the limited number of binding sites on the antibody (e.g. 60*c*). There will thus be no antibody binding site(e.g. 60*c*) available to react with the specific antigen (e.g. 61*c*) at the discrete region (e.g. 65*c*) of the test site 45, and no color will form at the test site 45 which is specific for that analyte (e.g. 65*c*). Thus, the absence of a color at this particular test site (e.g. 65*c*) indicates that the sample 70 tested contains at least that analyte.

Each antigen (61*b–f*) is immobilized at a specified discrete region (65*b–f*) in the test site 45. This allows the user to determine which specific analyte or analytes is present in the sample 70 by determining at which specific binding region 65*b–f* of the test site 45 the color is absent.

In one embodiment, a panel of drugs of abuse may be qualitatively assayed using a test strip 10 incorporating cotinine as a mobile positive control analyte 80. The drugs in the panel may include amphetamine, barbiturates, benzodiazepines, cocaine, methadone, methamphetamine, morphine, phencyclidine, tetrahydrocannabinol, and tricyclic antidepressants. Cotinine is a surrogate of these analytes, that is, cotinine is closely related to the analytes in terms of molecular weight and solubility, and is present at microgram concentrations. Cotinine does not cross react with any of these drugs, and the presence of any one or a combination of these drugs will not affect the reaction of the positive control analyte 80. Furthermore, even if cotinine was present in the urine to be tested, for example, in the urine of a heavy cigarette smoker, this endogenous cotinine would not affect the results at the positive control site.

Cotinine as a mobile control analyte 80 is incorporated into the sample pad 15 of the test strip 10. It may be incorporated at any location on the sample pad 15 or conjugate pad 35 as long as the migrating stream of sample 70 contacts the mobilizable cotinine analyte 80 and anti-cotinine antibody 60a before the sample 70 contacts the site containing immobilized cotinine as an immobilized control analyte 61*a*. In use, the liquid sample 70 solubilizes cotinine 80 then, upon contact with the conjugate pad 35, cotinine 80 saturates the binding sites on the anti-cotinine antibody 60*a*, which is bound to the gold particles 55. When the anti-cotinine 60a and cotinine 80 complex reaches the membrane 20, there is no anti-cotinine antibody binding site 61a that is available to react with the cotinine antigen 61a, and thus no color will form at the positive control site 65a. The lack of color formation is a positive result and indicates a functional positive control and assay. A positive result will be obtained regardless of the presence or absence of any other substance in the urine sample.

Use of the inventive positive control incorporated into the test strip offers many advantages. One advantage is that the positive control shares the same immunochemistry, mechanics and exposure as the sample to be tested. Accordingly, any malfunction of the analytical test may affect this "built-in" positive control to the same extent as the sample. For example, conditions affecting the test strip performance, such as improper storage temperature, use beyond the expiration date, etc., may affect the positive control, allowing the anti-cotinine 60a coated gold particles 55 to bind and produce a color at the positive control site. The formation or retention of color at the positive control site indicates the test is flawed. These results are likely inaccurate and should not be relied upon.

A positive control that is assayed using a system with the identical immunochemical reaction, the identical device and an analyte that is closely related to but non-crossreactive with one or more biological analytes of interest in a rapid assay system has not heretofore been accomplished with other kits containing a built in positive control.

The present invention overcomes the above-described drawbacks and provides a valid assessment of test performance and user competence. The positive control analyte, such as cotinine, is selected based on its lack of clinical or diagnostic significance in such assays and its non-crossreactivity with the biological analyte of interest. Because the inventive test is based on specific antibody-antigen interactions, the presence of the positive control analyte will not affect other tests. By incorporating the positive control analyte into the test device itself, no additional effort, cost or time is required by the operator to obtain a result that both provides information concerning the analyte or analytes of interest, as well as the proper immunochemical and mechanical functioning of the test device and performance by the test operator.

It should be understood that the compositions and methods of the present invention shown and described in the specification are only preferred embodiments of the inventor who is skilled in the art and are not limiting in any way. For example, the test device may encompass just the individual strip as would be used in a clinical laboratory, or may include a housing such as used in tests for over-the-counter sale, or may be part of a cassette containing a number of test strips encased in one housing. As described, a negative control may also be included in the assay, in which color present at a negative control site in the test strip membrane would aid in verifying a functional assay. Various changes, modifications or alterations to these embodiments may therefore be made or resorted to without departing from the spirit of the invention and the scope of the following claims.

What is claimed is:

1. A test strip for immunoassay of at least one biological analyte in a sample comprising, in order of sample migration, a sample pad, a conjugate pad, a membrane containing a test site wherein the presence of said analyte in said sample is indicated by absence of color formation at said test site, said strip comprising a mobile positive control analyte immunologically distinct from said biological analyte in said sample pad, a labeled antibody specific to said control analyte in said conjugate pad, a labeled antibody specific to at least one of said biological analyte in said conjugate pad, an immobile control analyte at a positive control site in said membrane, and an immobile biological analyte at said test site in said membrane, said test strip indicating immunoassay function by absence of color formation at said control site, and said test strip indicating presence of said biological analyte at said test site by the absence of color formation at said test site.

2. The test strip of claim 1 wherein the control analyte is selected from the group consisting of cotinine, creatinine, digoxin and combinations thereof.

3. The test strip of claim 1 further comprising a negative control analyte.

4. The test strip of claim 1 further comprising a dye at said positive control site.

5. The test strip of claim 1 wherein the antibody has a label selected from the group consisting of an enzyme, a metal sol, a chromophore, a fluorophore and combinations thereof.

6. The test strip of claim 1 contained in a housing.

7. A plurality of the test strips of claim 1 contained in a housing.

8. A test strip for concurrent immunoassay of a biological analyte in a sample and a control analyte by competitive immunoassay, said test strip comprising a sample pad comprising a mobilizable control analyte immunologically distinct from said biological analyte, a conjugate pad comprising a mobilizable labeled antibody to said control analyte and a mobilizable labeled antibody to said biological analyte, and a downstream membrane comprising a discrete region of immobilizable control analyte and a discrete region of immobilized biological analyte.

9. The test strip of claim 8, wherein said control analyte is cotinine.

10. The test strip of claim 8, wherein said biological analyte is at least one drug.

11. The test strip of claim 8, wherein said discrete region of immobilizable control analyte contains a marker dye.

* * * * *